(12) United States Patent
Kamme et al.

(10) Patent No.: US 7,354,742 B2
(45) Date of Patent: Apr. 8, 2008

(54) METHOD FOR GENERATING AMPLIFIED RNA

(75) Inventors: Fredrik Kamme, San Diego, CA (US); Jessica Y. Zhu, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 895 days.

(21) Appl. No.: 10/080,795

(22) Filed: Feb. 22, 2002

(65) Prior Publication Data

US 2003/0175714 A1    Sep. 18, 2003

(51) Int. Cl.
*C12P 19/34* (2006.01)
*C12Q 1/68* (2006.01)

(52) U.S. Cl. .................. 435/91.2; 435/6; 435/91.1

(58) Field of Classification Search .............. 435/91.1, 435/91.2, 6, 4, 5, 7.1, 288; 536/24.3, 23.4; 436/501

See application file for complete search history.

(56) References Cited

U.S. PATENT DOCUMENTS

| | | | |
|---|---|---|---|
| 4,683,195 | A |  7/1987 | Mullis et al. |
| 4,683,202 | A |  7/1987 | Mullis |
| 5,716,785 | A |  2/1998 | Van Gelder et al. |
| 5,814,506 | A * |  9/1998 | Kong et al. ............ 435/194 |
| 6,271,002 | B1 * |  8/2001 | Linsley et al. ........... 435/91.1 |
| 6,406,891 | B1 * |  6/2002 | Legerski ................ 435/91.1 |
| 6,436,677 | B1 * |  8/2002 | Gu et al. ............... 435/91.2 |
| 6,566,502 | B1 * |  5/2003 | Mack et al. ............. 530/350 |
| 6,783,940 | B2 * |  8/2004 | McLaughlin et al. ........ 435/6 |
| 7,186,507 | B2 * |  3/2007 | Bacallao et al. ........... 435/6 |

FOREIGN PATENT DOCUMENTS

| | | |
|---|---|---|
| EP | 0 682 121 A1 | 11/1995 |
| EP | 1 103 624 A1 |  5/2001 |
| WO | 91/02814 A1 |  3/1991 |
| WO | 00/75356 A1 | 12/2000 |

OTHER PUBLICATIONS

Aliotta et al., "Thermostable Bst DNA polymerase I lacks a 3'-->5' proofreading exonuclease activity," Genetic Analysis: Biomolecular Engineering, 1996, vol. 12, pp. 185-195.*
Chee et al., "Accessing Genetic Information with High-Density DNA Arrays", *Science* (1996) 274(5287): 610-614.
Chirgwin et al., "Idolation of Biologically Active Ribonucleic Acid from Sources Enriched in Ribonuclease", *Biochem.* (1979) 18(24): 5294-5299.
DeRisi et al., "Exploring the Metabolic and Genetic Control of Gene Expression on a Genomic Scale", *Science* (1997) 278(5338): 680-686.
Ferguson et al., "A Fiber-Optic DNA Biosensor Microarray for the Analysis of Gene Expression", *Nature Biotechnol.* (1996) 14(12): 1681-1684.
Ueli Gubler and Beth J. Hoffman, "A Simple and Very Efficient Method for Generating cDNA Libraries", *Gene* (1983) 25(2-3):263-269.
Han et al., "Quantum-Dot-Tagged Microbeads for Multiplexed Optical Coding of Biomolecules", *Nature Biotechnol.* (2001) 19(7): 631-635.
Lashkari et al., "Yeast Microarrays for Genome Wide Parallel Genetic and Gene Expression Analysis", *P.N.A.S. USA* (1997) 94(24): 13057-13062.
Andrew Marshall and John Hodgson, "DNA chips: An Array of Possibilities", *Nature Biotechnol.* (1998) 16(1): 27-31.
Graham Ramsay, "DNA Chips: State-of-the-Art", *Nature Biotechnol.* (1998) 16(1): 40-44.
Gobinda Sarkar and Steve S. Sommer, "Access to a Messenger RNA Sequence or its Protein Product is Not Limited by Tissue or Species Specificity", *Science* (1989) 244(4902): 331-334.
Mark Schena, "Genome Analysis with Gene Expression Microarrays", *BioEssays* (1996) 18(5): 427-431.
Schena et al., "Parallel Human Genome Analysis: Microarray-Based Expression Monitoring Of 1000 Genes", *P.N.A.S. USA* (1996) 93(20): 10614-10619.
Schena et al., "Quantitative Monitoring of Gene Expression Patterns with a Complementary DNA Microarray", *Science* (1995) 270(5235): 467-470.
Shalon et al., "A DNA Microarray System for Analyzing Complex DNA Samples Using Two-Color Fluorescent Probe Hybridization", *Genome Research* (1996) 6(7):639-645.
Stoflet et al., "Genomic Amplification with Transcript Sequencing", *Science* (1988) 239(4839): 491-494.
Xu et al., "Identification of Differentially Expressed Genes in Human Prostate Cancer Using Subtraction and Microarray", *Cancer Research*, vol. 60, pp. 1677-1682 (2000).
Cestari, I. N. et al., "A PCR shortcut to oocyte expression," *Biotechniques*, 1993, 14(3), pp. 404, 406-407.

* cited by examiner

*Primary Examiner*—Young J. Kim
(74) *Attorney, Agent, or Firm*—Woodcock Washburn LLP (57) ABSTRACT

The present invention provides a new method for producing amplified RNA from a selected set of cells. This method combines and utilizes known methods in a novel way to produce the gene expression profiles. The methods of the present invention utilize thermostable DNA polymerases and RNase H to produce high fidelity second strand synthesis of nucleic acids from selected cells in a highly efficient mariner and in substantially reduced time.

21 Claims, 3 Drawing Sheets

SEQUENCE LISTING

```
<160> NUMBER OF SEQ ID NOS: 3

<210> SEQ ID NO 1
<211> LENGTH: 67
<212> TYPE: DNA
<213> ORGANISM: Artificial Sequence
<220> FEATURE:
<223> OTHER INFORMATION: Synthetic Construct

<400> SEQUENCE: 1
tctagtacct gcttcactgc atctaatacg actcactata gggagatttt tttttttttt      60
tttttt                                                                 67

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
agatgaccta ggatgggagg                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gtgtgcactg tgattcagac                                                  20
```

METHOD FOR GENERATING AMPLIFIED RNA

BACKGROUND OF THE INVENTION

Gene expression is important for understanding a wide range of biological phenomena, including development, differentiation, senescence, oncogenesis, and many other medically important processes. Recently, changes in gene expression have also been used to assess the activity of new drug candidates and to identify new targets for drug development. The latter objective is accomplished by correlating the expression of a gene or genes known to be affected by a particular drug with the expression profile of other genes of unknown function when exposed to that same drug; genes of unknown function that exhibit the same pattern of regulation, or signature, in response to the drug are likely to represent novel targets for pharmaceutical development.

Generally, the level of expression of the protein product of a gene and its messenger RNA (mRNA) transcript are correlated, so that measuring one provides you with reliable information about the other. Since in most instances it is technically easier to measure RNA than to measure protein, variations in mRNA levels are commonly employed to assess gene expression in different cells and tissues or in the same cells and tissues at different stages of disease or development or exposed to different stimuli. One particularly useful method of assaying gene expression at the level of transcription employs DNA microarrays (Ramsay et al., *Nature Biotechnol.* (1998) 16:40-44; Marshall and Hodgson, *Nature Biotechnol.* (1998) 16:27-31; Lashkari et al., *P.N.A.S. USA* (1997) 94:130-157; and DeRisi et al., *Science* (1997) 278:680-686).

Mammalian cells contain as many as $1 \times 10^5$ to $3 \times 10^5$ different mRNA molecules, each of which varies in abundance (or frequency) within a given cell. The most abundant mRNAs are typically present at many thousands of copies per cell, while others may be present in as few as one copy or less per cell. Techniques for analyzing gene expression at the level of transcription typically require tens to hundreds of micrograms of mRNA, or as much as might be found in $10^7$-$10^9$ mammalian cells. Oftentimes, it is impractical to obtain this number of cells from a tissue of interest. For example, a blood sample typically contains $10^6$ nucleated cells/ml; hence, to obtain $10^9$ cells for analysis would necessitate taking a 1000 ml blood sample, which is clearly impractical in most instances.

Various methods have been described in the literature for amplifying the amount of a nucleic acid, such as deoxyribonucleic acid (DNA) and RNA, present in a sample. Among these, the most widely practiced is the polymerase chain reaction (PCR), described in U.S. Pat. No. 4,683,195 by Mullis et al., entitled "Process for Amplifying, Detecting, and/or Cloning Nucleic Acid Sequences," issued 28 Jul. 1987 and U.S. Pat. No. 4,683,202 by Mullis, entitled "Process for Amplifying Nucleic Acid Sequences," issued 28 Jul. 1987, and herein incorporated by reference. Briefly, PCR consists of amplifying denatured, complementary strands of target nucleic acid by annealing each strand to a short oligonucleotide primer, wherein the primers are chosen so as to flank the sequence of interest. The primers are then extended by a polymerase enzyme to yield extension products that are themselves complementary to the primers and hence serve as templates for synthesis of additional copies of the target sequence. Each successive cycle of denaturation, primer annealing, and primer extension essentially doubles the amount of target synthesized in the previous cycle, resulting in exponential accumulation of the target.

PCR methodologies in general suffer from several limitations that are well known in the art; see U.S. Pat. No. 5,716,785 by Van Gelder et al., entitled "Processes for Genetic Manipulations Using Promoters," issued 10 Feb. 1998) and *PCR Protocols: A Guide to Methods and Applications*, (Innis et al. (Ed.) Academic Press Inc., San Diego, Calif., 1990) for review and discussion of limitations. One such limitation is that different cDNAs may be amplified with different efficiencies, resulting in under-representation of some cDNA sequences and overrepresentation of others in the amplified product. Even a small difference in efficiency may result in a several-thousand fold differential in the representation of these cDNAs in the product after only thirty cycles of amplification. An attempt at using PCR to globally amplify all cDNAs in a sample for gene expression profiling reported an unacceptable degree of variability.

An alternative method of mRNA amplification is known as in vitro transcription (IVT) and is described in U.S. Pat. No. 5,716,785 by Van Gelder et al., entitled "Processes for Genetic Manipulations Using Promoters," issued 10 Feb. 1998, which is herein incorporated by reference. Unlike PCR, IVT does not result in geometric amplification, but rather in linear amplification. In IVT, an oligo(dT) primer that is extended at the 5'-end with a bacteriophage T7 RNA polymerase promoter (RNAP) is used to prime the poly-A+ mRNA population for cDNA synthesis. After synthesis of the first-strand cDNA, the second-strand cDNA is made using the method of Gubler and Hoffman (*Gene* (1983) 25:263-269). Addition of RNA polymerase results in in vitro transcription and linear amplification of mRNA that is anti-sense to the poly-A+ RNA.

Two other types of nucleotide amplification are described in Stoflet et al., *Science* (1988) 239:491-494) and in Sarkar and Sommer, *Science* (1989) 244:331-334). Stoflet et al. describes a variation of PCR known as genomic amplification with transcript sequencing (GAWTS). In GAWTS, a phage promoter is attached to at least one of the two PCR primers. The DNA segments amplified by PCR are transcribed to further increase signal and to provide an abundance of single-stranded template for reverse transcriptase-mediated dideoxy sequencing. Sarkar and Sommer (1989) supra, describes a modification of the GAWTS method, known as RNA amplification with transcript sequencing (RAWTS). RAWTS consists of four steps:
(i) cDNA synthesis with oligo(dT) or an mRNA-specific oligonucleotide primer,
(ii) PCR where one or both oligonucleotides contains a phage promoter attached to a sequence complementary to the region to be amplified,
(iii) transcription with a phage promoter, and
(iv) reverse transcriptase-mediated dideoxy sequencing of the transcript, which is primed with a nested (internal) oligonucleotide.

Both the GAWTS and RAWTS methods, however, involve relatively large numbers of PCR cycles, e.g. twenty-seven rounds (Stoflet et al. (1988) supra) or forty rounds (Sarkar and Sommer (1989) supra). As described above, large numbers of PCR cycles suffer from different efficiencies of amplification, and ensuing variability There exists a need in the art for improved methods of amplifying nucleic acids, especially mRNA, which methods can achieve a high degree of amplification from a limited amount of mRNA and which are reproducible. New improved methods for amplifying nucleic acids are also needed in the art that reduce the time required to perform the amplification process and greatly improve the efficiency of amplification. Such new improved methods would greatly facilitate the rapid processing of clinical samples, and would also be amenable to automation, which would provide substantial commercial advantages for medical and diagnostic applications. The present invention is believed to satisfy these needs and to provide other related advantages.

Citation of a reference herein shall not be construed as an admission that such reference is prior art to the present invention.

SUMMARY OF THE INVENTION

The present invention relates to methods for amplification of nucleic acids using new improved methods for amplification of RNA derived from cells, preferably eukaryotic cells and most preferably mammalian cells, which methods are reproducible and enable amplification of extremely small amounts of mRNA, such as might be obtained from as few as tens to hundreds of mammalian cells. In typical embodiments of the invention, a thermostable DNA polymerase is used in the second strand synthesis step. The use of a thermostable DNA polymerase enables the generation of a relatively large amount of RNA from a small starting number of cells with high efficiency, and in a substantially reduced time period compared to the known methods for performing RNA amplification. RNAs generated using this method may be labeled and employed to profile gene expression in different populations of cells.

In one embodiment, the invention is directed to a method for amplifying at least one mRNA in a sample containing a plurality of different mRNAs comprising:
 a) synthesizing first strand nucleic acid molecules by contacting under conditions conducive to reverse transcription activity at least one mRNA in said sample with:
  (i) reverse transcriptase, and
  (ii) (ii) a first primer that is sufficiently complementary to a sequence in the mRNA so as to prime synthesis in a direction toward the 5' end of the mRNA;
 b) synthesizing a double-stranded nucleic acid molecule by contacting under conditions conducive to thermosilable DNA polymerase activity the first strand synthesis step with:
  (i) a first thermostable DNA polymerase, and
  (ii) a thermostable RNAse H;
 c) transcribing resultant double stranded nucleic acid molecules into cRNA by contacting the double stranded nucleic acid molecules with an RNA polymerase under conditions conducive to RNA polymerase activity, such that cRNA is produced.

In another embodiment, the invention is directed to the above amplifying method, further comprising, after the transcribing step, determining the presence or absence of a pre-selected target mRNA in said sample.

In a specific embodiment, the invention is directed to an amplifying method, wherein the mRNA is extracted from at least one cell of interest, and further comprising contacting the cRNA produced with an array containing one or more species of polynucleotide positioned at pre-selected sites on the array, under conditions conducive to hybridization; and detecting any hybridization that occurs between the one or more species of polynucleotide and the cRNA.

In another embodiment, the invention is directed to a method for comparing the presence or amount of at least one mRNA of interest in a first sample and in a second sample, said first sample and said second sample each containing a plurality of different mRNAs from one or more cells, comprising, for the first sample, (a) synthesizing first strand nucleic acid molecules by contacting under conditions conducive to reverse transcription activity at least one mRNA in said sample with (i) reverse transcriptase, and (ii) a first primer that is sufficiently complementary to a sequence in the mRNA so as to prime synthesis in a direction toward the 5' end of the mRNA; (b) synthesizing a double-stranded nucleic acid molecule by contacting under conditions conducive to thermostable DNA polymerase activity the first strand synthesis step with (i) a first thermostable DNA polymerase, and (ii) a thermostable RNase H and (c) transcribing resultant double stranded nucleic acid molecules into cRNA by contacting the double stranded nucleic acid molecules with an RNA polymerase under conditions conducive to RNA polymerase activity, such that cRNA is produced; (d) labeling the cRNA produced in step c) with a first label; (e) repeating steps (a)-(c) with said second sample; (f) labeling the cRNA produced in step (e) with a second label distinguishable from said first label; (f) detecting or measuring the mRNA of interest in the first sample by contacting the cRNA labeled with said first label with a polynucleotide probe capable of hybridizing to said cRNA of the mRNA of interest under conditions conducive to hybridization; and detecting any hybridization that occurs between said probe and said cRNA; (g) detecting or measuring the mRNA of interest in the second sample by contacting the cRNA labeled with said second label with said polynucleotide probe capable of hybridizing to said cRNA of the mRNA of interest under conditions conducive to hybridization; and detecting any hybridization that occurs between said probe and said cRNA; and (h) comparing the mRNA of interest detected or measured in said first sample with the mRNA of interest detected or measured in said second sample.

In a specific embodiment of the above method, in steps (f) and (g), the steps of contacting the cRNA labeled with said first label with said polynucleotide probe, and contacting the cRNA labeled with said second label with said polynucleotide probe, are carried out concurrently.

In another specific embodiment of the method described above, the first sample contains mRNAs from cells that are pathologically aberrant, and the second sample contains mRNAs from cells that are not pathologically aberrant.

In another embodiment, the invention is directed to a kit comprising in one or more containers (a) a mixture of first primers; (b) a thermostable DNA polymerase; and (c) a thermostable RNase H.

In another embodiment of the invention, a label or labels may be introduced into the RNA during the transcription step to facilitate gene expression profiling in different populations of cells.

BRIEF DESCRIPTION OF THE DRAWINGS

| Lane A: | E. Coli DNA pol. I ten minutes, 37° C. |
|---|---|
| Lane B: | E. Coli DNA pol. I thirty minutes, 37° C. |
| Lane C: | E. Coli DNA pol. I sixty minutes, 37° C. |
| Lane D: | Bst pol. thirty minutes, 42° C. |
| Lane E: | Bst pol. thirty minutes, 50° C. |
| Lane F: | Bst pol. thirty minutes, 55° C. |
| Lane G: | Bst pol. thirty minutes, 60° C. |

| | |
|---|---|
| Lane A: | Bst pol. 65° C./ten minutes |
| Lane B: | *E. Coli* DNA pol. I 16° C./two hours |
| Lane C: | *E. Coli* DNA pol. I 37° C./one hour |
| Lane D: | Klenow 37° C./one hour |

DETAILED DESCRIPTION OF THE INVENTION

The present invention provides methods for the amplification of nucleic acid sequences in a population of cells, which methods are reproducible and enable the amplification of extremely small amounts of mRNA, such as might be obtained from as few as a single mammalian cell.

It is to be understood that the invention is not limited to the particular embodiments described below, as variations of the described embodiments may fall within the enclosed claims. Also, the terminology used to describe the enclosed embodiments is not intended to be limiting. The scope of the present invention is established by the claims.

As described above, this invention provides method for amplifying nucleic acids. Nucleic acids are polymers consisting of ribonucleotides or deoxyribonycleotides, or a mixture of both. 'RNA' is a polymer, consisting of ribonucleotides, and at least two nucleotides long, but generally longer, usually 100-10000 nucleotides. 'DNA' is a polymer, consisting of deoxyribonucleotides, and at least two nucleotides long, but generally longer, usually 100-10000 nucleotides. cDNA is a DNA polymer synthesized using an RNA polymer as a template, therefore containing the complementary sequence of the RNA polymer. An oligonucleotide is a short DNA or RNA polymer, or a mixture of both. Oligonucleotides are at least two nucleotides long, more usually 10-150 nucleotides. The oligonucleotide primer for use in the methods of the present invention can be of any suitable size, and are preferably 40-100 nucleotides in length. The oligonucleotide primers can be DNA, chimeric mixtures of RNA and DNA or derivatives or modified versions thereof, so long as it is still capable of priming the desired reaction. The oligonucleotide primer can be modified at the base moiety, sugar moiety, or phosphate backbone, and may include other appending groups or labels, so long as it is still capable of priming the desired amplification reaction. The oligonucleotide primers may be derived by cleavage of a larger nucleic acid fragment using non-specific nucleic acid cleaving chemicals or enzymes or site-specific restriction endonucleases; or by synthesis by standard methods known in the art, e.g. by use of an automated DNA synthesizer (such as are commercially available from Biosearch, Applied Biosystems, etc.) and standard phosphoramidite chemistry.

The methods of the invention are applicable to nucleic acid sequences derived from both eukaryotic and prokaryotic cells, although they are preferably used with eukaryotic cells, and most preferably, with mammalian cells. Among cells that may serve as sources of DNA or RNA are nucleated blood cells, established cell lines, tumor cells, and tissue biopsy specimens, normal tissues, organs, as well as pathologically aberrant cells, among others that will be readily apparent to those of skill in the art. Pathologically aberrant cells include cells involved directly or indirectly with a disease or condition, such as infected cells, cells that have become abnormal, cancerous cells, cells producing a substance that causes a disease or condition, or cells that produce or fail to produce a particular protein or proteins inconsistently with normal cells. Cells from which nucleic acid molecules are to be derived may be collected using a wide variety of techniques well known in the art, including, but not limited to, laser capture using instrumentation, reagents and instructions supplied by, for example Arcturus, PALM, or Leica manufacturers, aspiration of cells or the intracellular contents of living or preserved cells using micropipettes, needle or surgical biopsies, cell sorting, such as fluorescence activated cell sorting, or by antibody binding sorting. Cells of interest also include wild-type cells, drug-exposed wild-type cells, modified cells, and drug-exposed modified cells.

Although the amplification methods of the invention can be adapted to amplify DNA, it is preferred to utilize the methods to amplify RNA from a population of cells. Total cellular RNA, cytoplasmic RNA, or poly(A)+ RNA may be used. Methods for preparing total and poly(A)+ RNA are well known and are described generally in Sambrook et al., *Molecular Cloning—A Laboratory Manual*, $2^{nd}$ *Edition*, (Cold Spring Harbor Laboratory, Cold Spring Harbor, N.Y., 1989, Vol. 1-3) and *Current Protocols in Molecular Biology*, (Ausubel et al. (Eds.), Current Protocols Publishing, NY, 1994, Vol. 2).

RNA may be isolated from eukaryotic cells by a wide variety of procedures known in the art that involve lysis of the cells and denaturation of the proteins contained therein. Additional steps may be employed to remove DNA. Cell lysis may be accomplished with a nonionic detergent, followed by microcentrifugation to remove the nuclei and hence the bulk of the cellular DNA. RNA may be extracted from cells of the various types of interest using guanidinium thiocyanate lysis followed by CsCl centrifugation to separate the RNA from DNA (Chirgwin et al., *Biochem.* (1979) 18:5294-5299). Poly(A)+ RNA is selected by selection with oligo-dT cellulose (see Sambrook et al., *Molecular Cloning—A Laboratory Manual*, $2^{nd}$ *Edition*, (Cold Spring Harbor Laboratory, Cold Spring Harbor, N.Y., 1989, Vol. 1-3). Alternatively, separation of RNA from DNA can be accomplished by organic extraction, for example, with acid phenol or phenol/chloroform/isoamyl alcohol. Alternatively, RNA may be extracted from samples based on binding of RNA to silica under chaotropic conditions. If desired, RNase inhibitors may be added to the lysis buffer. Likewise, for certain cell types, it may be desirable to add a protein denaturation/digestion step to the protocol.

The sample of RNA can comprise a plurality of different mRNA molecules, each different mRNA molecule having a different nucleotide sequence. In a specific embodiment, the mRNA molecules in the RNA sample comprise 100 or fewer different nucleotide sequences. More typically, the mRNA molecules of the RNA sample comprise less than 500, or up to 100,000 or more different nucleotide sequences. The mRNA molecules of a mammalian RNA sample may possibly contain about 20,000 to 30,000 or more different nucleotide sequences.

Total RNA or mRNA from cells is used in the methods of the present invention. The source of the RNA can be from a wide variety of cells, including, but not limited to, cells of a plant or animal, human, mammal, primate, non-human animal, dog, cat, mouse, rat, bird, yeast, eukaryote, or prokaryote.

In the method of this invention, cDNA is enzymatically synthesized from mRNA, primed by an oligonucleotide that carries in the 5' end the sequence for an RNA polymerase promoter, such as T7 RNA polymerase. The resulting single-stranded cDNA is converted into double-stranded cDNA using a mix of a DNA polymerase and an RNase H. The double-stranded cDNA is then transcribed using T7 RNA polymerase, or other RNA polymerases, producing RNA. Several RNA molecules will be transcribed for each template cDNA molecule, thus constituting an amplification step. The produced RNA is called amplified RNA. Using high-yield transcription kits, such as the Ampliscribe kit from Epicentre (Madison, Wis.), it is possible to achieve 500-3000 fold amplification judged by mass.

In the method of this invention, the first-strand cDNA is preferably produced by reverse transcription, wherein DNA is made from RNA using the enzyme reverse transcriptase. Reverse transcriptase is found in all retroviruses and is commonly obtained from avian myeloblastoma virus or Moloney murine leukemia virus; enzyme from these sources is commercially available from Invitrogen and Roche.

In general, it is preferred to use the poly(A) tail of mRNA for reverse transcription, using an oligo(dT)-containing primer. The primer will preferably contain about twelve to thirty T nucleotides, most preferably twenty-one T nucleotides. In a specific embodiment, the primer for reverse transcription contains between 35-100 T nucleotides.

The primer for first strand cDNA synthesis is an oligo dT primer with the RNA polymerase promoter sequence in the 5' end that primes synthesis in the direction towards the 5' end of substantially all the mRNAs in the sample. The primer may be prepared by any suitable methods, such as phosphotriester and phosphodiester methods of synthesis, or automated embodiments thereof. It is also possible to use a primer that has been isolated from a biological source, such as a restriction endonuclease digest, although synthetic primers are preferred. A wide variety of RNA polymerase promoter sequences are suitable for use in the methods of the present invention and are well known to those skilled in the art, including, but not limited to, T7, T3 and Sp6 promoters.

The primer for first strand cDNA synthesis is annealed to the RNA in water. 5 ng to 5000 ng, preferably 10 ng to 500 ng, more preferably 25 ng to 200 ng of primer is mixed with RNA. The mixture is added to a temperature between 60° C. and 90° C., preferably about 70° C., for about five minutes and then cooled on ice. cDNA is synthesized using a reverse transcriptase, preferably RNase H- such as Superscript II (Invitrogen), in a buffer containing 50 mM Tris-HCl, 75 mM KCl, 3 mM MgCl$_2$, 20 mM dithiothreitol, 500 µM deoxynucleotide triphosphates (dNTPs) in a volume of approximately 20 µL. Forty units RNasin (Promega) may be added to protect RNA from RNase contamination. Typical amounts of Superscript II reverse transcriptase is 200 units/reaction. The mix is incubated preferably between 37° C. and 42° C. for one to two hours.

In the method of the present invention, a substantial and unexpected improvement has been made to the second strand cDNA synthesis step by the usage if thermostable enzymes. In the methods of the present invention, enzymes are considered thermostable and suitable for use herein if they maintain enzymatic activity above 50° C., and are referred to herein as "thermostable DNA polymerases". Previous to the discovery of the improvements of the present invention, second strand synthesis methods are carried out by a method known in the art. In the previous methods used in the art, the DNA polymerase used for second strand cDNA synthesis were typically E. coli DNA polymerase I, Klenow fragment of E. coli DNA polymerase I, or T4 DNA polymerase. The most frequently used method to date is the Gubler-Hoffman method originally described in 1983 (Gubler and Hoffman (1983) supra), in which E. coli DNA polymerase I, RNase H and E. coli DNA ligase I is used.

By way of example, but not limitation, second strand cDNA synthesis is generally performed in the current invention by adding an aliquot of the first strand cDNA reverse transcribed above into a mix containing 20 mM Tris-HCl pH 8.8, 10 mM KCl, 10 mM (NH$_4$)$_2$SO$_4$, 2 mM MgSO$_4$, 0.1% Triton X-0.100, 375 µM dNTPs, 24 U of Bst DNA polymerase large fragment (New England Biolabs), five units of thermostable RNase H ('Hybridase', Epicentre, Wis.) and water to a final volume of 80 µl and incubated at temperature of 65° C. for ten minutes. The temperature of incubation is preferably 45° C. to 80° C., more preferably 55° C. to 70° C., and most preferably 60° C. to 65° C. The time of incubation is one to sixty minutes, more preferably five to thirty minutes, and most preferably ten to twenty minutes. The concentration of Bst DNA polymerase large fragment is preferably 0.012 to 1.3 units/µl, more preferably 0.12 to 0.63 units per/µl, and most preferably 0.18 to 0.44 units/µl. The concentration of thermostable RNase H is preferably 0.0031 units/µl to 1.3 units/µl, more preferably 0.0062 units/µl to 0.63 units/µl, and most preferably 0.012 to 0.32 units/µl.

Other thermostable DNA polymerases than Bst DNA polymerase large fragment may be employed and are suitable for use in the methods of the present invention for second strand cDNA synthesis at an elevated temperature above 45° C. Suitable thermostable DNA polymerases include, but not limited to, Bst DNA polymerase native enzyme, Taq DNA polymerase, Pfu DNA polymerase, Tgo DNA polymerase, Phi29 DNA polymerase plus a thermostabilizing agent such as trehalose, T7 DNA polymerase plus a thermostabilizing agent such as trehalose, or the Klenow fragment of E. coli polymerase 1 plus a thermostabilizing agent such as trehalose, native E. coli DNA polymerase I plus a thermostabilizing agent such as trehalose.

After second strand cDNA synthesis, the cDNA may optionally be purified. Several options exist for purification. A preferred method is purifying the DNA on a silica column in chaotropic conditions, e.g. the PCRquick column (Qiagen). It is preferable to add 100 ng of polyinosinic acid to the sample to be purified to minimize adsorptive losses of materials during purification. The double-stranded cDNA carries a functional T7 RNA polymerase promoter and is transcribed using a high yield T7 RNA transcription kit such as the Ampliscribe kit (Epicentre) or the Megascribe kit (Ambion).

One cycle of first strand cDNA synthesis, second strand cDNA synthesis and RNA transcription as described above will yield an amplification of 500-3000 fold as judged by RNA mass. For some applications, in particular single cell samples, further amplification may be required. This can be done performing a second cycle of first strand cDNA synthesis, second strand cDNA synthesis and RNA transcription. Starting from amplified RNA, the RNA is heat denatured at 70° C. for ten minutes in the presence of 1 µg of random hexamers in water in a total volume of 10 µl. The mix is quench cooled on ice, and first strand cDNA synthesis mix, as described above, is added. The mix is incubated at room temperature for ten minutes before incubating at 37° C. for two hours. After incubation, 1 µl E. coli RNase H is added and the mix is incubated a further thirty minutes at 37°

C. to digest the RNA strand in the RNA-cDNA hybrid. The reaction is then heated to 95° C. for five minutes, and then cooled on ice. As the amplified RNA used as a template for the cDNA synthesis reaction contains three to six bases derived from the T7 RNA polymerase promoter followed by a stretch of uridines, the cDNA will end at the 3' end with a stretch of deoxyadenines plus the T7 RNA polymerase promoter derived bases. This sequence in the cDNA is exploited to prime the second strand synthesis by hybridizing the cDNA with the T7dT21 oligonucleotide used above. The heat-denatured cDNA is hybridized with 11 g T7dT21 oligonucleotide at 42° C. for ten minutes, and then cooled on ice. This serves as the template for second strand cDNA synthesis. Second strand cDNA synthesis can be performed using the Gubler-Hoffman method outlined above. Alternatively, Bst DNA polymerase large fragment can be used as described above. The temperature of incubation is preferably reduced to 60° C. The double-stranded cDNA is purified and transcribed using T7 RNA polymerase as described above.

We have observed that free $T7dT_{21}$ primer will result in transcription and the production of RNA if put into a T7 RNA transcription mix. This may be due to partial hybridization between two $T7dT_{21}$ oligonucleotides as part of the central promoter is canonical. If Bst DNA polymerase large fragment is used for second strand cDNA synthesis in the first cycle of first strand cDNA synthesis, second strand cDNA synthesis and T7 RNA transcription, and, all of the product is used for a second cycle of first strand cDNA synthesis, second strand cDNA synthesis and T7 RNA transcription, an RNA product will appear in negative controls. This effect is probably due to the lack of 5'-3' exonuclease activity in Bst DNA polymerase large fragment. This will result in $T7dT_{21}$ oligonucleotide remaining in solution after second strand cDNA synthesis, which then will carry over into the transcription reaction. The importance of this observation may be particularly relevant when very small samples of RNA are employed, such as single cell RNA samples. This effect can be greatly reduced by incubating the double-stranded cDNA after second strand cDNA synthesis with ten to fifteen units of E. coli Exonuclease I for fifteen minutes prior to purification of the cDNA. Alternatively, the effect can be prevented by designing the $T7dT_{21}$ primer in such a way that the tendency to from oligonucleotide dimers is reduced. Such a design may be that the 5' end of the $T7dT_{21}$ oligonucleotide forms a hairpin structure, with a mismatched terminal five to ten bases that sterically prevent the canonical part of the central promoter to hybridize in a $T7dT_{21}$ dimer. The steric effect for blocking dimers forming can be enhanced by conjugating a bulky group at the 5'-end of the oligonucleotide. By way of example, but not limitation, the bulky group may be a fluorophore such as Cy3.

The method of the present of the invention may be used to perform amplification in situ, on samples of preserved or fresh cells or tissues (see, e.g., PCR—In Situ Hybridization: Protocols and Applications, 3$^{rd}$ Edition, (Nuovo (Ed.) Lippincott-Raven Press, NY, 1997).

Nucleic acid amplification products such as amplified RNA, or cDNA synthesized from amplified RNA, may be labeled with any art-known detectable marker, including radioactive labels such as $^{32}$P, $^{35}$S, $^{3}$H, and the like; fluorophores; chemiluminescers; or enzymatic markers, with fluorescent labels preferred such as fluorescein isothiocyanate, lissamine, Cy3, Cy5, and rhodamine 110, with Cy3 and Cy5 particularly preferred. Suitable fluorophore moieties that can be selected as labels include, but are not limited to, 4-acetamido-4'-isothiocyanatostilbene-2,2'disulfonic acid acridine and derivatives: acridines, acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), -(4-anilino-1-naphthyl)maleimide, anthranilimide, Brilliant Yellow, coumarin and derivatives: coumarin, 7-amino-4-methylcoumarin (AMC, Coumarin 120), 7-amino-4-trifluoromethylcoumarin (Coumarin 151), Cy3, Cy5, cyanosine, 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), eosin and derivatives: eosin, eosin isothiocyanate, erythrosin and derivatives: erythrosin B, erythrosin isothiocyanate, ethidium, fluorescein and derivatives: 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate, QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene and derivatives: pyrene, pyrene butyrate, succinimidyl 1-pyrene butyrate, Reactive Red 4 (Cibacron.RTM. Brilliant Red 3B-A), rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 110, rhodamine 123, rhodamine X isothiocyanate, sulforhodamine B, sulforhodamine 101, sulfonyl chloride derivative of sulforhodamine 101 (Texas Red), N,N,N'N'-tetramethyl-6-carboxyrhodamine (TAMRA), tetramethyl rhodamines, tetramethyl rhodamine isothiocyanate (TRITC), riboflavin, rosolic acid, terbium chelate derivatives.

Not only fluorophores, but also chemiluminescers and enzymes, among others, may be used as labels. In yet another embodiment, the RNA or cDNA may be labeled with an enzymatic marker that produces a detectable signal when a particular chemical reaction is conducted, such as alkaline phosphatase or horseradish peroxidase. Such enzymatic markers are preferably heat stable, so as to survive the second strand synthesis and denaturing steps of the amplification process of the present invention.

RNA amplified by the methods of this invention is suitable for quantitative comparisons of gene expression between different populations of cells or between populations of cells exposed to different stimuli. The invention utilizes the ability to measure the responses of a biological system to a large variety of perturbations. One of ordinary skill in the art would appreciate that this invention is not limited to the following specific methods for measuring the responses of a biological system. In particular, the presence of cRNA(s) of interest (and thus mRNA(s) of interest in the sample) can be detected or measured by procedures including, but not limited to, Northern blotting or using bead-bound oligonucleotides as probes, or the use of polynucleotide microarrays.

One or more labels is introduced into the RNA during the transcription step to facilitate gene expression profiling. Gene expression can be profiled in any of several ways, among which the preferred method is to probe a DNA microarray with the labeled RNA transcripts generated above. A nucleic acid microarray, or chip, is a microscopic array of nucleic acids, such as DNA fragments or synthetic oligonucleotides, disposed in a defined pattern on a solid support, wherein they are amenable to analysis by standard hybridization methods (Schena et al., *BioEssays* (1996) 18: pg. 427).

The nucleic acid in a microarray may be derived from genomic or cDNA libraries, from fully sequenced clones, from partially sequenced cDNAs known as expressed sequence tags (ESTs), or synthetically made on the microarray surface or substrate. Methods for obtaining such DNA molecules are generally known in the art (see, e.g., *Current Protocols in Molecular Biology*, (Ausubel et al. (Eds.), Current Protocols Publishing, NY, 1994, Vol. 2). Alternatively, oligonucleotides may be synthesized by conventional methods, such as phosphoramidite-based synthesis.

Gene expression profiling can be done for a wide variety of purposes, including but not limited to, screening, diagnosis, staging a disease, and monitoring response to therapy, as well as for identifying genetic targets of drugs and of pathogens.

This invention is particularly useful to produce aRNA for the analysis of gene expression profiles, in particular for diagnostic applications. For expression profiling, nucleic acid microarrays are typically probed using nucleic acid molecules, extracted and amplified from the cells whose gene expression profile it is desired to analyze, using the amplification method of the present invention. To facilitate comparison between any two samples of interest, the nucleic acid molecules are typically labeled separately with fluorescent dyes that emit at different wavelengths, as described herein. Some embodiments of this invention are based on measuring the transcriptional rate of genes.

The transcriptional rate can be measured by techniques of hybridization to arrays of nucleic acid or nucleic acid mimic probes, or by other gene expression technologies. However measured, the result is either the absolute, relative amounts of transcripts or response data including values representing RNA abundance ratios, which usually reflect DNA expression ratios (in the absence of differences in RNA degradation rates). In various alternative embodiments of the present invention, aspects of the biological state other than the transcriptional state, such as the translational state, the activity state, or mixed aspects can be measured. Preferably, measurement of the transcriptional state is made by hybridization to transcript arrays, which are described in this subsection. Certain other methods of transcriptional state measurement are described later in this subsection.

Nucleic acid molecules made using the method of the present invention may be used in "transcript arrays" (also called herein "microarrays"). Transcript arrays can be employed for analyzing the transcriptional state in a biological sample and especially for measuring the transcriptional states of a biological sample exposed to graded levels of a drug of interest or to graded perturbations to a biological pathway of interest. Transcript arrays are produced by hybridizing detectably labeled polynucleotides representing the mRNA transcripts present in a cell (e.g., fluorescently labeled cRNA that is amplified by the methods of the present invention) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain preferred characteristics: The arrays are reproducible, allowing multiple copies of a given array to be produced and easily compared with each other. Preferably the microarrays are small, usually smaller than 5 cm$^2$, and they are made from materials that are stable under binding (e.g., nucleic acid hybridization) conditions. A given binding site or unique set of binding sites in the microarray will typically specifically bind the product of a single gene in the cell.

A microarray is typically an array of polynucleotides, the array comprising a support with at least one surface and multiple different polynucleotides, each different polynucleotide comprising a different nucleotide sequence and being attached to the surface of the support in a different location on the surface. Preferably, the nucleotide sequence of each of the different polynucleotide probes is in the range of about 20 to 1000 or more nucleotides in length. The array typically comprises polynucleotides of more than one different sequence, but can have many more, such as 2,000, 4,000, 10,000, 15,000, 20,000, 50,000, 80,000, 100,000 or more different nucleotide sequences.

The nucleotide sequence of each polynucleotide in the array may be specific for a particular counterpart or complementary polynucleotide sequence. The target polynucleotide sequences may also comprise expressed polynucleotide sequences of a cell or organism. The nucleotide sequences of the different polynucleotides of the array may be specific for one or more of the genes in the entire genome of the cells to be analyzed. Nucleic acid arrays may have more than one, or many thousands of nucleic acid molecules per 1 cm$^2$, and are typically arranged as a positionally addressable array, in that the sequence of the nucleic acid molecules at each position is known. The nucleic acid molecule in the array may be DNA or RNA.

When cRNA complementary to the RNA of a cell is made and hybridized to the nucleic acid molecules in a microarray under suitable hybridization conditions, the level of hybridization to the site in the array corresponding to any particular nucleotide sequence will reflect the prevalence in the cell of mRNA transcribed from the gene corresponding to that sequence. For example, when detectably labeled (e.g., with a fluorophore) cRNA complementary to the total cellular mRNA is hybridized to the nucleic acid molecules of a microarray, the site on the array corresponding to a particular gene that is not transcribed in the cell will have little or no signal (e.g., fluorescent signal), and a gene for which the encoded mRNA is prevalent will have a more detectable signal. Additionally, cRNAs from two different cells are hybridized to the nucleic acid molecules of the microarray. In the case of drug responses one biological sample is exposed to a drug and another biological sample of the same type is not exposed to the drug. In the case of pathway responses one cell is exposed to a pathway perturbation and another cell of the same type is not exposed to the pathway perturbation. The cRNA derived from each of the two cell types are differently labeled so that they can be distinguished, for example, cRNA from a cell treated with a drug (or exposed to a pathway perturbation) is synthesized using a fluorescein-labeled NTP, and cRNA from a second cell, not drug-exposed, is synthesized using a rhodamine-labeled NTP. When the two cRNAs are mixed and hybridized to the microarray nucleic acids, the relative intensity of signal from each cRNA set is determined for each site on the array, and any relative difference in abundance of a particular mRNA detected.

In the example described above, the cRNA from the drug-treated (or pathway perturbed) cell will fluoresce green when the fluorophore is stimulated and the cRNA from the untreated cell will fluoresce red. As a result, when the drug treatment has no effect, either directly or indirectly, on the relative abundance of a particular mRNA in a cell, the mRNA will be equally prevalent in both cells and, upon reverse transcription, red-labeled and green-labeled cRNA will be equally prevalent. When hybridized to the microarray, the binding site(s) for that species of RNA will emit wavelengths characteristic of both fluorophores. In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Schena et al., *Science* (1995) 270:467-470, which is incorporated by reference in its entirety for all purposes. An advantage of using cRNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cRNA from a single cell, and compare, for example, the absolute amount of a particular mRNA in, e.g., a drug-treated or pathway-perturbed cell and an untreated cell.

Microarrays are known in the art and consist of a surface to which probes that correspond in sequence to gene products (e.g., cDNAs, mRNAs, cRNAs, polypeptides, and fragments thereof), can be specifically hybridized or bound at a known position. The microarray may be an array (i.e., a matrix) in which each position represents a discrete binding site for a product encoded by a gene (e.g., a protein or RNA), and in which binding sites are present for products of most or almost all of the genes in the organism's genome. The "binding site" (hereinafter, "site") is a nucleic acid or nucleic acid analogue to which a particular cognate cRNA can specifically hybridize. The nucleic acid or analogue of the binding site can be, e.g., a synthetic oligomer, a full-length cRNA, a less-than full length cRNA, or a gene fragment.

Nucleic acid hybridization and wash conditions are optimally chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. It can easily be demonstrated that specific hybridization conditions result in specific hybridization by carrying out a hybridization assay including negative controls (see, e.g., Shalon et al., *Genome Research* (1996) 6:639-645 and Chee et al., *Science* (1996) 274:610-614). Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., *Molecular Cloning—A Laboratory Manual*, $2_{nd}$ Edition, (Cold Spring Harbor Laboratory, Cold Spring Harbor, N.Y., 1989, Vol. 1-3) and in *Current Protocols in Molecular Biology*, (Ausubel et al. (Eds.), Greene Publishing, Media, P A and Wiley-Interscience, NY, 1987). When the cDNA microarrays of Schena et al. (*P.N.A.S. USA* (1996) 93:10614-10619) are used, typical hybridization conditions are hybridization in 5×SSC plus 0.2% SDS at 65° C. for four hours followed by washes at 25° C. in low stringency wash buffer (1×SSC plus 0.2% SDS) followed by ten minutes at 25° C. in high stringency wash buffer (0.1.times.SSC plus 0.2% SDS) (Schena et al., (1996) supra). Useful hybridization conditions are also provided in, e.g., *Hybridization With Nucleic Acid Probes*, (Tijssen et al., (Ed.) Elsevier Science Publishers B.V., The Netherlands and NY, USA, 1993) and *Nonisotopic DNA Probe Techniques*, (Kricka et al., (Ed.) Academic Press, San Diego, Calif., 1992).

Although simultaneous hybridization of differentially labeled mRNA samples is preferred, it is also possible to use a single label and to perform hybridizations sequentially rather than simultaneously.

When fluorescent labeled probes are used, the fluorescence emissions at each site of a transcript array can be, preferably, detected by scanning confocal laser microscopy. In one embodiment, a separate scan, using the appropriate excitation line, is carried out for each of the fluorophores used. Alternatively, a laser can be used that allows simultaneous specimen illumination at wavelengths specific to the fluorophores and emissions from the fluorophores can be analyzed simultaneously (see Shalon et al. (1996) supra, which is incorporated by reference in its entirety for all purposes). The arrays may be scanned with a laser fluorescent scanner with a computer controlled X-Y stage and a microscope objective. Sequential excitation of the fluorophores is achieved with a multi-line, mixed gas laser and the emitted light is split by wavelength and detected with multiple photomultiplier tubes. Fluorescence laser scanning devices are described in Shalon et al. (1996) supra and in other references cited herein. Alternatively, the fiber-optic bundle described by Ferguson et al., *Nature Biotechnol.* (1996) 14:1681-1684, may be used to monitor mRNA abundance levels at a large number of sites simultaneously.

Signals are recorded and analyzed by computer, e.g., using a twelve-bit analog to digital board. The scanned image may be despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the fluorophores can be calculated. The ratio is independent of the absolute expression level of the cognate gene, but is useful for genes whose expression is significantly modulated by drug administration, gene deletion, or any other tested event or cause.

Relative abundance of mRNA in the biological samples is scored as a perturbation and its magnitude determined (i.e., the abundance is different in the two sources of mRNA tested), or as not perturbed (i.e., the relative abundance is the same). A difference between the sources of RNA of at least a detectable level, such as a factor of about 25% (RNA from one source is 25% more abundant in one source than the other source), more usually about 50%, even more often by a factor of about two (twice as abundant), three (three times as abundant) or five (five times as abundant) is scored as a perturbation.

In addition to identifying a perturbation as positive or negative, it is advantageous to determine the magnitude of the perturbation. This can be carried out, as noted above, by calculating the ratio of the emission of the fluorophores used for differential labeling, or by analogous methods that will be readily apparent to those of skill in the art.

As an example, two samples, each labeled with a different fluor, are hybridized simultaneously to permit differential expression measurements. If neither sample hybridizes to a given spot in the array, no fluorescence will be seen. If only one hybridizes to a given spot, the color of the resulting fluorescence will correspond to that of the fluor used to label the hybridizing sample (for example, green if the sample was labeled with Cy3, or red, if the sample was labeled with Cy5). If both samples hybridize to the same spot, an intermediate color is produced (for example, yellow if the samples were labeled with fluorescein and rhodamine). Then, applying methods of pattern recognition and data analysis known in the art, it is possible to quantify differences in gene expression between the samples. Methods of pattern recognition and data analysis are well known to those skilled in the art.

The amplified RNA, or cDNA synthesized there from, may be used for expression analysis using other platforms than DNA microarrays. Arrays of polynucleotides can be made using addressable microspheres [Han et al., Nat Biotechnol. (2001) 19:631-635], where addresses may be created by a combination of fluorescing materials, such as fluorescent compounds or fluorescent nanoparticles. One set of microspheres carrying a unique address is created by loading that set of microspheres with a unique combination of fluorescent materials. The address is decoded by imaging the microspheres, e.g. with a color CCD camera, and quantifying the fluorescence at different wavelengths. The combination of colors and intensity of each color can be modulated to create a detectable address. By creating 10-100,000 optical addresses in such a way, a fluid array can be created, where each specific polynucleotide is immobilized on one type of microspheres carrying one particular optical address. If 100,000 optical addresses were created, it would be possible to analyze 100,000 different specific polynucleotides by hybridization analysis. The microspheres carrying polynucleotides representing sequences of interest are mixed and hybridized with labeled amplified RNA, or cDNA synthesized thereof. The label used for labeling amplified RNA, or cDNA synthesized thereof, may be fluorescent, radioactive, based on light scattering, using fluorescent nanoparticles or enzymatic. A preferable label is fluorescent or nanoparticle labeling. One benefit of hybridizing an array based on microspheres instead of a planar microarray is that the volume of hybridization can be dramatically reduced. A planar microarray containing 10,000 spots, representing potentially 10,000 individual sequences, requires normally 50-100 microliters of hybridization buffer to cover the surface. If we assume ten microspheres are utilized per address, 10,000 sequences would require 100,000 microspheres, which could be hybridized in less than 1 microliter, assuming that the size of each microsphere is 10 micrometer in diameter or less. The reduction in hybridization volume will likely enhance hybridization efficiency dramatically.

An additional aspect of the present invention relates to kits for the detection or measurement of nucleic acid amplification products and for determining the responses or state of a biological sample. In specific embodiments, the kits comprise one or more thermostable DNA polymerases as used in the method of the present invention, such as Taq DNA polymerase, Bst DNA polymerase large fragment, Bst DNA polymerase native enzyme, Pfu DNA polymerase, Tgo DNA polymerase, Phi29 DNA polymerase plus a thermostabilizing agent such as trehalose, T7 DNA polymerase plus a thermostabilizing agent such as trehalose, or the Klenow fragment of E. coli polymerase 1 plus a thermostabilizing agent such as trehalose, in one or more containers. The kit can further comprise additional components for carrying out the amplification reactions of the invention. Where the target nucleic acid sequence being amplified is one implicated in disease or disorder, the kits can be used for diagnosis or prognosis. In a specific embodiment, a kit is provided that comprises, in one or more containers, an oligonucleotide primer for carrying out amplification, a reverse transcriptase and optionally, a DNA polymerase, a thermostable RNase H.

Oligonucleotides in containers can be in any form, e.g., lyophilized, or in solution (e.g., a distilled water or buffered solution), etc. Oligonucleotides ready for use in the same amplification reaction can be combined in a single container or can be in separate containers. The kit optionally further comprises a set of directions for carrying out transcribing of amplified double-stranded cDNA into cRNA. The kit optionally further comprises a control nucleic acid, and/or a microarray, and/or means for stimulating and detecting fluorescent light emissions from fluorescently labeled RNA, and/or expression profile projection and analysis software capable of being loaded into the memory of a computer system.

Another example is a kit for the detection of a selected target DNA target sequence comprises in one or more containers (a) primers, and optionally: (b) a control DNA target sequence; (c) an optimized buffer for amplification; (d) appropriate enzymes for the method of amplification contemplated, e.g., a thermostable DNA polymerase for second strand synthesis; (d) a set of directions for carrying out amplification, e.g., describing the optimal conditions, e.g., temperature and time. Such kits may further contain expression profile projection and analysis software capable of being loaded into the memory of a computer system.

The following experimental examples are provided to illustrate the present invention and not to be considered to limit the present invention thereto.

EXAMPLE 1

2nd Strand cDNA Synthesis Starting from Total RNA

For second strand cDNA synthesis, we used the Gubler-Hoffman method as a reference point. This is a very well established method for synthesizing the second cDNA strand that uses a mix of E.Coli DNA polymerase I, Rnase H and DNA ligase I. It generates RNA oligomers from the mRNA strand in the mRNA-cDNA hybrid produced from the first strand cDNA synthesis, and uses these as primers for the second strand synthesis. We titrated temperature and time of incubation using E. Coli DNA polymerase I and Bst polymerase.

First Strand cDNA Synthesis 100 ng of total rat brain RNA was mixed with 500 ng of $T_7dT_{21}$ primer (5'-TCTAGTACCTGCTTCACTG-CATCTAATACGACTCACTATAGG-GAGATTTTTTTTTTTTT TTTTTTTT-3') (SEQ ID NO: 1) in a total volume of 11 µl. The mix was denatured at 70° C. for ten minutes and put on ice. cDNA was synthesized using 200 units SuperScript II reverse transcriptase (Invitrogen) in 50 mM Tris-HCl, 75 mM KCl, 3 mM $MgCl_2$, 20 mM dithiothreitol, 500 µM dNTPs and 40 units RNasin (Promega) in a 20 ul reaction for 2 hours at 42° C. The was terminated by incubating at 70° C. for ten minutes. When starting from amplified RNA, the aRNA was mixed with 1 µg of random hexamers (Amersham-Pharmacia Biotech) and denatured at 70° C. for ten minutes. cDNA synthesis was performed as above, except incubation was done at 37° C. for two hours.

Second Strand Synthesis Using E.Coli DNA Polymerase 1 (Gubler-Hoffman Method)

To the first strand reaction, the following was added: 30 µl of 5× second strand cDNA synthesis buffer (100 mM Tris-HCl pH 6.9, 23 mM MgCl2, 450 mM KCl, 0.75 mM β-NAD+, 50 mM (NH$_4$)$_2$SO$_4$), 3 µl of 10 mM dNTPs, 10 units E.Coli DNA ligase (Invitrogen), 40 units E.Coli DNA polymerase I (Invitrogen), 2 units Rnase H (Invitrogen) in a final volume of 150 µl. The mix was incubated at the designated temperature for the designated period of time. 2 µl of T4 DNA polymerase was then added and the mix was further incubated at 16° C. for fifteen minutes. The reaction was terminated by incubating at 70° C. for ten minutes. 100 ng of polyinosinic acid (Sigma) was added to each sample, and then 750 µl of PB buffer (Qiagen). The samples were purified on a PCR purification column (Qiagen) according to the manufacturer's directions. The DNA was eluted in 30 µl 1 mM Tris-HCl pH 8.0.

Second Strand Synthesis Using Bst Polymerase

To the first strand reaction, the following was added: 8 µl of Bst polymerase buffer (200 mM Tris-HCl pH 8.8, 100 mM KCl, 100 mM (NH$_4$)$_2$SO$_4$, 20 mM MgSO$_4$, 1% Triton X-100), 3 ul of 10 mM dNTPs, 24 U of Bst DNA polymerase large fragment (New England Biolabs), 5 units of thermostable RNase H (Epicentre) and water to a final volume of 80 µl. The mix was incubated at the designated temperature for the designated period of time. The reaction was terminated by incubating at 80° C. for fifteen minutes. 100 ng of polyinosinic acid (Sigma) was added to each reaction. 400 µl of PB buffer (Qiagen) was added and the samples were purified on a PCR purification column (Qiagen) according to the manufacturer's directions. The DNA was eluted in 30 µl 1 mM Tris-HCl pH 8.0.

Second Strand Synthesis Using the Klenow Fragment of E.Coli DNA Polymerase I

To the first strand reaction, the following was added: 3 µl of 10 mM dNTPs, 2 units Rnase H (Invitrogen), 8 µl of 10× Klenow buffer (100 mM Tris-HCL pH 7.5, 50 mM MgCl$_2$, 75 mM dithiothreitol) and 50 units of Klenow polymerase (New England Biolabs) in a final volume of 80 µl. The mix was incubated at the designated temperature for the designated period of time. The reaction was terminated by incubating at 80° C. for fifteen minutes, and purified as above.

Real-Time PCR Analysis

For PCR analysis, 2 µl of the purified double-stranded cDNA was used per reaction in a mix containing 3 mM MgCl$_2$ (added), 500 nM forward and reverse primer for rat neuron specific enolase (5'-AGATGACCTAGGATGG-GAGG-3', (SEQ ID NO: 2) 5'-GTGTGCACTGTG ATTCA-GAC-3') (SEQ ID NO: 3), 2 µl of Sybr Green I mix (Roche) premixed with 0.16 µl TaqStart antibody (Clontech) in a volume of 20 µl. The PCR reaction was run in a Lightcycler PCR machine (Roche).

T7 RNA Polymerase Transcription

The remainder of the double-stranded cDNA was dried down to 8 µl in a SpeedVac. The double stranded cDNA was transcribed using T7 RNA polymerase In a volume of 20 µl containing 2 µl 10× T7 transcription buffer, 1.5 µl each of ATP, CTP, GTP and UTP, 2 µl 0.1M dithiothreitol and 2 µl of T7 RNA polymerase. All reagents in the transcription reaction were from Epicentre's 'Ampliscribe' T7 Transcription kit. The transcription reaction was carried out for three hours at 42° C. 1 µl of DNase I was added and incubated a further fifteen minutes at 37° C. 100 ng of polyinosinic acid was added to the samples, which were then purified using Qiagen's Rneasy kit. Aliquots of the purified RNA products were run on a 1% agarose gel containing 1M urea.

Results

The temperature and time of incubation for Bst polymerase, E.Coli DNA polymerase I and Klenow was titrated, and the amount of double-stranded cDNA produced was quantified by real-time PCR.

TABLE 1

PCR Data of Second Strand cDNA Yield

| Enzyme for 2$^{nd}$ Strand cDNA Synthesis | Temperature for 2$^{nd}$ Strand Synthesis | Time of Incubation | 1$^{st}$ run PCR Data: Cross-Over Cycle* | 2$^{nd}$ Run PCR Data: Cross-Over Cycle* |
|---|---|---|---|---|
| Bst pol. | 60° C. | 10 min | 18.79 | 19.34 |
| Bst pol. | 65° C. | 10 min | | 18.63 |
| Bst pol. | 65° C. | 30 min | | 18.50 |
| Bst pol. | 65° C. | 60 min | | 18.92 |
| Bst pol. | 65° C. | 120 min | | 18.73 |
| E. Coli DNA pol I | 16° C. | 120 min | 19.26 | 20.12 |
| E. Coli DNA pol I | 37° C. | 60 min | 18.77 | |
| E. Coli DNA pol I | 37° C. | 120 min | 19.10 | |
| Klenow | 37° C. | 60 min | 20.03 | |
| Klenow | 37° C. | 120 min | 20.31 | |

*PCR samples were run in triplicates. The reported cross over cycle is thus an average of three data points.

In Table 1 the PCR data of the double-stranded cDNA is shown. Due to the number of samples and the limited capacity of the Lightcycler, the samples were split into two groups. Reported values are cross-over cycles, which signifies the cycle at which the fluorescence in the sample exceeds a chosen background level that is equal for all the samples. From previous experiments we know that the PCR efficiency for the NSE primer pair is approximately 0.95, thus a one cycle difference in cross-over cycle corresponds to approximately a 1.93-fold difference in starting amount of template. From the first PCR run, it is evident that Bst pol. ten minutes at 60° C. (cross-over cycle 18.79) and E. Coli DNA pol 1 sixty minutes at 37° C. (cross-over cycle 18.77) gave the highest yields of cDNA. In the second PCR run, Bst polymerase gave higher yields of cDNA at 65° C. than at 60° C. Already at ten minutes, the yield of cDNA using Bst at 65° C. was optimal. Remarkably, the yield of cDNA using Bst at 65° C. was three-fold higher than using E. Coli DNA polymerase 1 for two hours at 16° C. (Average cross-over cycle for Bst ten minutes and thirty minutes at 65° C. was 18.57; difference in cross-over cycles to E. Coli DNA polymerase 1 two hours at 16° C. was 20.12-18.57=1.55; with a PCR efficiency of 0.95 this represents a three-fold difference in input template.)

A selection of the conditions above was chosen for T7 RNA polymerase transcription. The RNA produced is in the antisense orientation and thus referred to as aRNA.

TABLE 2 aRNA Yields

| 2$^{nd}$ strand cDNA synthesis method | Average RNA yield* (µg) |
|---|---|
| Bst pol. 10 min at 65° C. | 12.4 |
| E. Coli DNA pol. I, 2 h at 16° C. | 4.85 |
| E. Coli DNA pol. I, 1 h at 37° C. | 6.30 |
| Klenow, 1 h at 37° C. | 4.06 |

*RNA transcription reactions were run in triplicates. Thus each RNA yield value is the average of three samples.

The final aRNA yields after T7 transcription in Table 2 support the PCR data. The order of aRNA yields were Bst pol. ten minutes at 65° C.>>E. Coli DNA pol I one hour at 37° C.>E. Coli DNA pol. I two hours at 16° C.>Klenow one hour at 37° C. This is identical to the order of the PCR data. Also, the increase in RNA yield between Bst pol. ten minutes at 65° C. and E. Coli DNA pol I two hours at 16° C. is very close to the increase seen in cDNA as measured by PCR (2.6 vs. 2.9). This shows that the increase seen in cDNA yields represents functional template for T7 RNA polymerase transcription.

Figure 2:
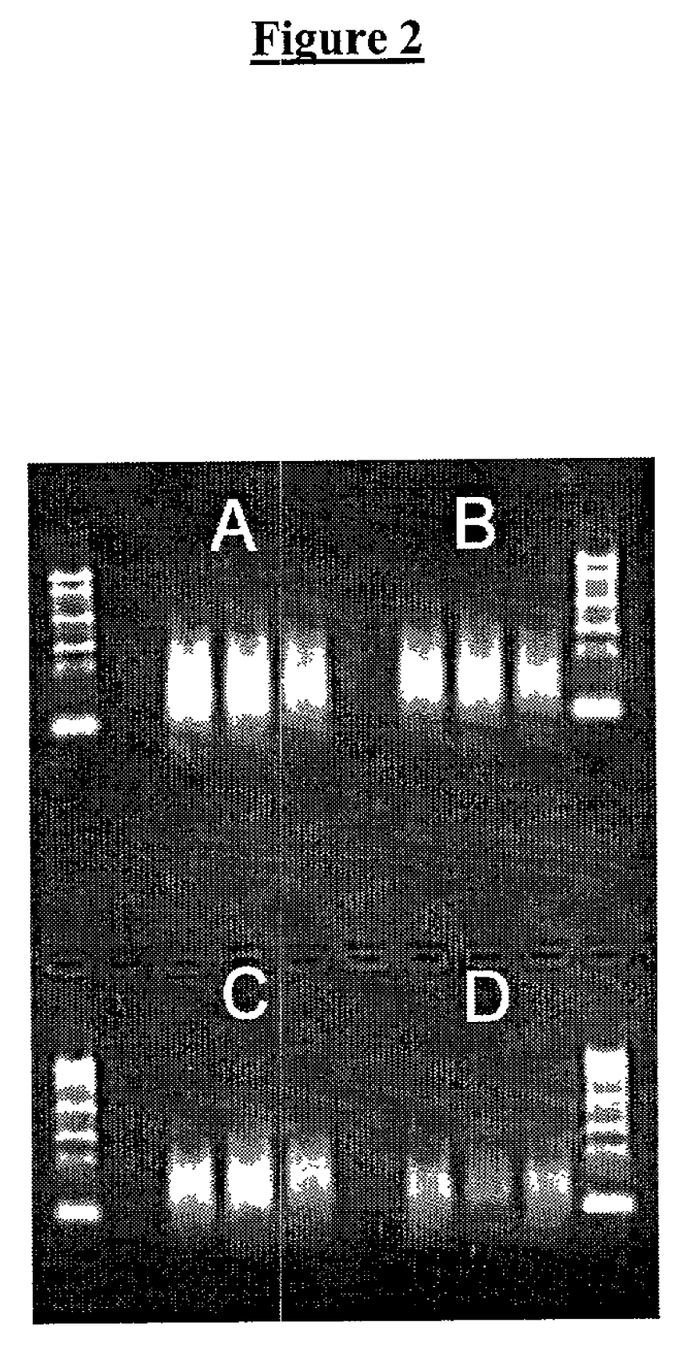
FIG. 2: aRNA samples run on a 1% denaturing agarose gel is shown. Conditions used for second strand cDNA synthesis.

Aliquots of the aRNA Samples Were Run on a Denaturing Agarose Gel (FIG. 2).

Figure 1:
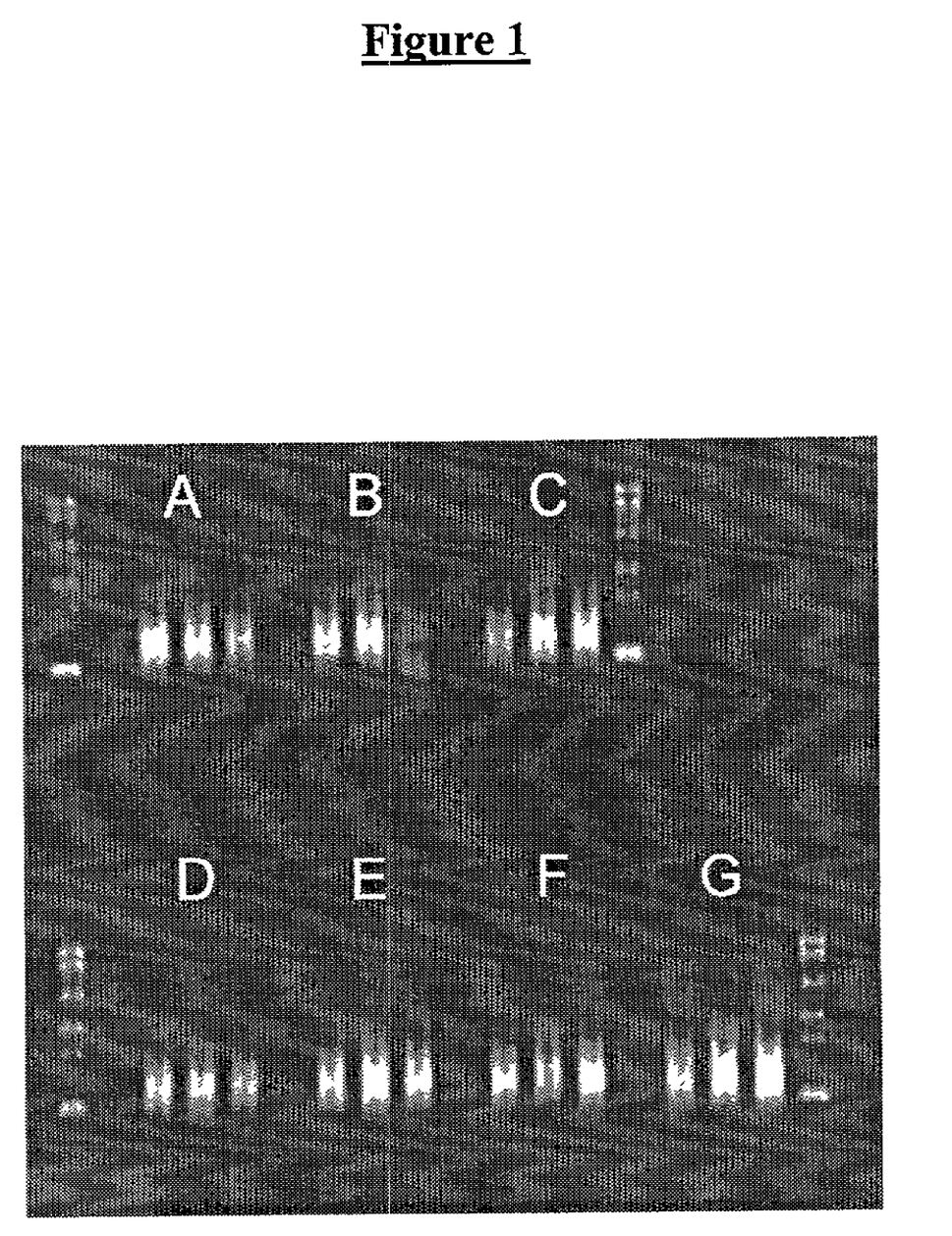
FIG. 1: Gel electrophoresis of aRNA products is shown

The image of the RNA gel in FIG. 1 clearly shows that using Bst polymerase at 65° C. for ten minutes gave increased amounts of aRNA as compared to using E. Coli DNA polymerase, either at 16° C. for two hours or at 37° C. for one hour. Use of Klenow resulted in relatively poor yields of aRNA. The size distribution is between 240 and 3000 bases for all samples, which is the normal distribution of RNA products from T7 RNA polymerase transcription of a complex template. Also, the negative control, which was run to the left of the triplicate samples, was blank for all conditions.

To further quantify the generated aRNA products, 1:15$^{th}$ of the aRNA was used to synthesize first strand cDNA. The cDNA was diluted 1:50 and analyzed by PCR as described above.

TABLE 3

PCR data of 1$^{st}$ strand cDNA from aRNA.

| 2$^{nd}$ strand cDNA synthesis method | PCR cross-over cycle |
| --- | --- |
| Bst pol. 10 min at 65° C. | 17.87 |
| E. Coli DNA pol. I, 2 h at 16° C. | 18.87 |
| E. Coli DNA pol. I, 1 h at 37° C. | 18.59 |
| Klenow, 1 h at 37° C. | 20.05 |

Values are averages of triplicate samples.

The PCR data in Table 3 corroborate the RNA yields in Table 2. Bst polymerase at 65° C. for ten minutes gave significantly higher yields of cDNA than either condition using E. Coli DNA polymerase I, showing that the increase in RNA yield is reflected in an increase in the number of transcripts.

Conclusion

The data show that by using Bst polymerase and thermostable RNase H for generating second strand cDNA, the yields of double stranded cDNA increases significantly as compared to using the conventional method, namely E.Coli DNA polymerase 1, Rnase H and E.Coli DNA ligase as originally described by Gubler and Hoffman. In addition to the increased yield, the reaction time is shortened from 2.5 hours to ten minutes.

EXAMPLE 2

Second Strand cDNA Synthesis from aRNA

The aRNA produced by T7 RNA amplification can be used as the input RNA for an additional round of T7 RNA amplification. The aRNA produced in the first round is in the antisense orientation and thus lacks any known sequence in the 3'-end. The cDNA synthesis from aRNA is therefore primed using random hexamers. To regenerate the T7 RNA polymerase promoter site, the aRNA-cDNA hybrid is then denatured and second strand cDNA synthesis is primed using the T7dT$_{21}$ primer. This is a different way of synthesizing second strand cDNA to the first round of T7 RNA amplification where second strand cDNA synthesis is primed by RNA oligomers left by the RNase H activity. Therefore we set out to identify the optimal conditions for synthesizing second strand cDNA in the second round of T7 RNA amplification. First the temperature and time requirements were titrated using E. Coli DNA polymerase I. Then a similar set of experiments was done using Bst polymerase.

cDNA synthesis cDNA was synthesized from first round aRNA generated using Bst polymerase for second strand cDNA synthesis. 20 ng of one round aRNA was mixed with 1ug of random hexamers (Amersham-Pharmacia Biotech) and denatured at 70° C. for ten minutes. cDNA was synthesized in a volume of 20 µl containing 200 units Superscript II (Invitrogen), 50 mM Tris-HCl, 75 mM KCl, 3 mM MgCl$_2$, 20 mM dithiothreitol, 500 µM dNTPs and 40 units RNasin (Promega). The mix was incubated ten minutes at room temperature and then at 37° C. for two hours. The reaction was terminated by incubating at 70° C. for ten minutes and then put on ice. Two units of RNase H (Invitrogen) was added to the mix and incubated for twenty minutes at 37° C. The mix was then denatured for two minutes at 90° C. and put on ice. 0.5 µg of T$_7$dT$_{21}$ primer was added and the mix was incubated at 70° C. for ten minutes and then at 42° C. for ten minutes. Second strand cDNA was then synthesized either using E. Coli DNA polymerase I or Bst polymerase.

Second Strand Synthesis Using E. Coli DNA Polymerase I

To the first strand reaction, the following was added: 30 µl of 5x second strand cDNA synthesis buffer (100 mM Tris-HCl (pH 6.9), 23 mM MgCl2, 450 mM KCl, 0.75 mM β-NAD$^+$, 50 mM (NH$_4$)$_2$SO$_4$), 3 µl of 10 mM dNTPs, 20 units E. Coli DNA polymerase I (Invitrogen), two units RNase H (Invitrogen) in a final volume of 150 µl. The mix was incubated at the designated temperature for the designated period of time. Ten units of T4 DNA polymerase was then added and the mix was further incubated at 16° C. for fifteen minutes. The reaction was terminated by incubating at 70° C. for fifteen minutes. 100 ng of polyinosinic acid (Sigma) was added to each sample, and then 750 µl of PB buffer (Qiagen). The samples were purified on a PCR purification column (Qiagen) according to the manufacturer's directions. The DNA was eluted in 30 µl 1 mM Tris-HCl pH 8.0.

Second Strand Synthesis Using Bst Polymerase

To the first strand reaction, the following was added: 8 µl of Bst polymerase buffer (200 mM Tris-HCl pH 8.8, 100 mM KCl, 100 mM (NH$_4$)$_2$SO$_4$, 20 mM MgSO$_4$, 1% Triton X-100), 3 ul of 10 mM dNTPs, 24 units of Bst DNA polymerase large fragment (New England Biolabs), five units of thermostable RNase H (Epicentre) and water to a final volume of 80 μl. The mix was incubated at the designated temperature for the designated period of time. The reaction was terminated by incubating at 80° C. for fifteen minutes. 100 ng of polyinosinic acid (Sigma) was added to each reaction. 400 μl of PB buffer (Qiagen) was added and the samples were purified on a PCR purification column (Qiagen) according to the manufacturer's directions. The cDNA was eluted in 30 μl 1 mM Tris-HCl pH 8.0.

Second Strand Synthesis Using the Klenow Fragment of *E. Coli* DNA Polymerase I

To the first strand reaction, the following was added: 3 μl of 10 mM dNTPs, 2 units RNase H (Invitrogen), 8 μl of 10× Klenow buffer (100 mM Tris-HCL pH 7.5, 50 mM $MgCl_2$, 75 mM dithiothreitol) and 50 units of Klenow polymerase (New England Biolabs) in a final volume of 80 μl. The mix was incubated at the designated temperature for the designated period of time. The reaction was terminated by incubating at 80° C. for fifteen minutes, and purified as above.

Real-Time PCR Analysis

For PCR analysis, 2 μl of the purified cDNA was used per reaction in a mix containing 3 mM $MgCl_2$ (added), 500 nM forward and reverse primer for rat neuron specific enolase (5'-AGATGACCTAGGATGGGAGG-3' (SEQ ID NO: 2, 5'-GTGTGCACTGTGATTCAGAC-3', SEQ ID NO: 3), 2 μl of Roche Sybr Green I mix premixed with 0.16 μl TaqStart antibody (Clontech) in a volume of 20 μl. The PCR reaction was run in a Lightcycler PCR machine (Roche).

T7 RNA Polymerase Transcription.

The remainder of the double-stranded cDNA was dried down to 16 μl in a SpeedVac. The double-stranded cDNA was transcribed using T7 RNA polymerase In a volume of 40 μl containing 4 μl T7 transcription buffer, 3 μl each of ATP, CTP, GTP and UTP, 4 μl 0.1M dithiothreitol and 4 μl of T7 RNA polymerase. All reagents in the transcription reaction were from Epicentre's Ampliscribe T7 Transcription kit. The transcription reaction was carried out for 3 h at 42° C. Two units of DNase 1 was added and incubated a further fifteen minutes at 37° C. The resulting aRNA product was purified using Qiagen's Rneasy kit.

An aliquot of the purified aRNA product was run on a 1% agarose gel containing 1M urea. aRNA was quantified by measuring OD in a spectrophotometer (Beckman, DU-530). To further quantify the yield of RNA, cDNA was synthesized using random priming as described above. PCR analysis was performed as described above, except the template was diluted 1:50.

Results

The efficiency of second strand cDNA synthesis using *E. Coli* DNA polymerase I was evaluated at 16° C. and 37° C. Due to concerns about the 5'-3' exonuclease activity at 37° C., an 5'-3' exonuclease deficient fragment of *E. Coli* DNA polymerase I, the Klenow fragment, was tested in parallel.

TABLE 4

PCR Data

| Conditions for second strand cDNA synthesis in second round | PCR data Cross-over cycle |
|---|---|
| *E. Coli* DNA pol. I 16° C./2 h | 16.63 |
| *E. Coli* DNA pol. I 37° C./1 h | 16.78 |
| Klenow 37° C./1 h | 16.73 |

Cross-over cycle values are averages of triplicate measurements

In Table 4, the cross-over values from the PCR analysis of the different conditions are within the margins of error of the PCR method, signifying that the yield of cDNA is equal between *E. Coli* DNA pol. I 16° C./two hours, *E. Coli* DNA pol. I 37° C./one hour and Klenow 37° C./one hour.

TABLE 5 aRNA Yields Measured by OD

| Conditions for second strand cDNA synthesis in second round | aRNA yield (μg) |
|---|---|
| *E. Coli* DNA pol. I 16° C./2 h | 43.5 |
| *E. Coli* DNA pol. I 37° C./1 h | 39.6 |
| Klenow 37° C./1 h | 31.5 |

Values represent the average of triplicate samples

The cDNA templates generated above were transcribed using T7 RNA polymerase and quantified. The yield of aRNA, shown in Table 5, is equal for *E. Coli* DNA polymerase 16° C. for two hours and 37° C. for one hour. Klenow resulted in a comparable amount of aRNA.

The minimum time of incubation for second strand cDNA synthesis using *E. Coli* DNA polymerase I was then titrated. Double-stranded cDNA was generated from first round aRNA using *E. Coli* DNA polymerase I at 37° C. for ten, thirty or sixty minutes.

In the same experiment, the temperature of incubation for second strand cDNA synthesis was titrated using Bst polymerase at 42° C., 50° C., 55° C. or 60° C. for thirty minutes.

TABLE 6

PCR Data

| 2nd Strand cDNA Synthesis Protocol | Cross-Over Cycle |
|---|---|
| *E. Coli* DNA pol. 1 10 min, 37° C. | 17.62 |
| *E. Coli* DNA pol. 1 30 min, 37° C. | 17.75 |
| *E. Coli* DNA pol. 1 60 min, 37° C. | 17.82 |
| Bst pol. 30 min, 42° C. | 17.45 |
| Bst pol. 30 min, 50° C. | 17.13 |
| Bst pal. 30 min, 55° C. | 17.28 |
| Bst pol. 30 min, 60° C. | 17.29 |

Cross-over cycle values are the average of triplicate measurements

The amount of cDNA was measured by PCR as shown in Table 6. For *E. Coli* DNA polymerase I, ten minutes at 37° C. gave the same amount of cDNA as sixty minutes. For Bst polymerase, the differences in cross-over cycle values between the different incubation temperatures are within the margins of error.

TABLE 7

| 2nd Strand cDNA Ssynthesis Protocol | RNA Yield (μg) |
| --- | --- |
| E. Coli DNA pol. 1 10 min, 37° C. | 35.1 |
| E. Coli DNA pol. 1 30 min, 37° C. | 32.4* |
| E. Coli DNA pol. 1 60 min, 37° C. | 35.0 |
| Bst pol. 30 min, 42° C. | 32.0 |
| Bst pol. 30 min, 50° C. | 32.3 |
| Bst pol. 30 min, 55° C. | 29.2 |
| Bst pol. 30 min, 60° C. | 35.1 |

RNA yields are the average of triplicate measurements
*One outlier value was omitted The double-stranded cDNAs generated in the previous step were transcribed by T7 RNA polymerase and the resulting aRNA products were quantified by measuring OD. As seen in Table 7, for E. Coli DNA polymerase 1, there is no difference in aRNA yield between 10 and sixty minutes of incubation during the second strand cDNA synthesis. For Bst polymerase, the differences in aRNA yield between the different incubation temperatures are not significant.

The size distribution of the aRNA products generated in the previous step was normal for all the conditions tested. Also, the negative reactions run for each condition, located to the left of each triplet of samples on the gel, were all blank.

TABLE 8

| 2nd Strand cDNA Synthesis Protocol | Cross-Over Cycle |
| --- | --- |
| E. Coli DNA pol. 1 10 min, 37° C. | 18.54 |
| E. Coli DNA pol. 1 30 min, 37° C. | 18.54* |
| E. Coli DNA pol. 1 60 min, 37° C. | 18.84 |
| Bst pol. 30 min, 42° C. | 19.28 |
| Bst pol. 30 min, 50° C. | 18.67 |
| Bst pol. 30 min, 55° C. | 18.93 |
| Bst pol. 30 min, 60° C. | 18.79 |

Cross-over cycle values are the average of triplicate samples.
*Contains only two samples.

To further validate the aRNA yields in Table 7, first strand cDNA was synthesized and quantified by PCR. The cross-over cycle values in Table 8 support the aRNA yields in Table 7.

The temperature titration of second strand cDNA synthesis using Bst polymerase in the second round showed modest differences in aRNA yield as measured by OD and RT-PCR. We chose 55° C. and 60° C. for further study, as the enzyme (Bst polymerase) is likely to be more processive at higher temperatures. To determine the minimum time required for second stand cDNA synthesis in the second round using Bst polymerase, the reaction was performed at 55° C. and 60° C. for ten and thirty minutes.

TABLE 9

| Enzyme used for 2nd Strand cDNA Synthesis In second Round | Incubation Temperature | Time of Incubation | PCR cross-Over Cycle |
| --- | --- | --- | --- |
| E. Coli DNA pol. I | 37° C. | 10 min | 16.68* |
| Bst pol. | 55° C. | 10 min | 18.09 |
| Bst pol. | 55° C. | 30 min | 17.77 |
| Bst pol. | 60° C. | 10 min | 16.48 |
| Bst pol. | 60° C. | 30 min | 17.00 |

Cross-over cycle values from PCR analysis. Each value is the average of triplicate samples.
*average of two samples.

The PCR data in Table 9 show that the minimum time of incubation for using Bst polymerase to synthesize the second cDNA strand in the second round, with optimum yield, is ten minutes at 60° C. The yield compares favorably with the optimized conditions for using, E. Coli DNA polymerase for the same reaction. The double-stranded cDNA products were transcribed with T7 RNA polymerase and the purified aRNA products were quantified and run on a denaturing agarose gel.

TABLE 10 aRNA Yields

| Enzyme used for second strand cDNA synthesis in second round | Incubation temperature | Time of incubation | aRNA yield (μg) |
| --- | --- | --- | --- |
| E. Coli DNA pol. I | 37° C. | 10 min | 34.9 |
| Bst pol. | 60° C. | 10 min | 31.7 |
| Bst pol. | 60° C. | 30 min | 33.0 |

Values are averages of triplicate samples.

The aRNA yield data in Table 10 support the PCR data in Table 9. The amount of aRNA produced by the optimized Bst polymerase protocol is equivalent to the optimized protocol for E. Coli DNA polymerase I. Either enzyme can be used to make second strand cDNA in the second round of T7 amplification, with optimum efficiency in a ten minute reaction.

Conclusion

This set of experiments set out to identify the optimum conditions for synthesizing the second cDNA strand in the second round of T7 RNA amplification. The goal was to achieve maximal efficiency in the shortest possible incubation time. The standard method for synthesizing the second strand in cDNA synthesis, is to use a combination of E. Coli DNA polymerase I, Rnase H and DNA ligase, as described by Gubler and Hoffman (1983) supra. This method was used as a reference point in these experiments. We started out by titrating temperature and time of incubation when using E. Coli DNA polymerase 1. The results show that using E. Coli DNA polymerase I at 37° C. for ten minutes gave the same yield of cDNA and subsequent aRNA as using the same enzyme at 16° C. for two hours. The same set of optimizations was carried out with Bst polymerase and the results show that using Bst polymerase at 60° C. for ten minutes was as efficient as using E. Coli DNA polymerase.

EXAMPLE 3

Microarray Probe Synthesis

Cy3 labeled cDNA probes were synthesized from aRNA. In brief, 10 μg aRNA and 5 μg random hexamers were mixed in a total volume of 26 μl (containing RNase free $H_2O$), heated to 70° C. for 10 minutes and chilled on ice. Then, 10

μl first strand buffer, 5 μl 0.1MDTT, 1.5 μl RNasin. 1 μl 25 mM d(GAT)TP, 2 μl 1 mM dCTP, 2 μl 1 mM Cy3-dCTP (Amersham) and 2.5 μl Superscript RT II were added and incubated at room temperature for ten minutes and then 37° C. for two hours. To degrade the aRNA template, the sample was digested using 10 units of RNase H (Invitrogen) and 0.1 units of RNase A (Sigma) for ten minutes at 37° C. The samples were purified on PCRquick columns (Qiagen). The probes were vacuum dried and re-suspended in 50% formamide, 5× microarray hybridization buffer (Amersham Biosciences) in a total volume of 50 ml. The probe was denatured at 95° C. for ten minutes and then cooled on ice.

Microarray Hybridization and Washes

The hybridization probe was applied to the microarray, covered with a cover glass slide and the assembly was sealed with DPX (Fluka). The microarrays were hybridized at 42° C. for sixteen to eighteen hours. The cover glass was removed and the microarray was rinsed in 1×SSC/0.2% SDS at room temperature and then washed for ten minutes in 1×SSC/0.2% SDS at 55° C., ten minutes in 0.1×SSC 0.2% SDS at 55° C. with a final rinse in 0.1×SSC at room temperature. The microarrays were spun dry and scanned immediately in a Molecular Dynamics Generation III microarray scanner.

Microarray Quantitation.

ImaGene Software (Biodiscovery, Inc.) was used for quantitation. Briefly, the intensity of each spot (i.e., cDNA) was corrected by subtracting the immediate surrounding background. Next, the corrected intensities were normalized for each cDNA (i.e., spot) with the following formula: intensity (background corrected)/75-percentile value of the intensity of the entire chip x 1000. To determine "non-specific" nucleic acid hybridization, 75-percertile values were calculated from the individual averages of each plant cDNA (for a total of thirty different cDNAs) from each neuronal set.

Statistical Analyses.

Figure 3:
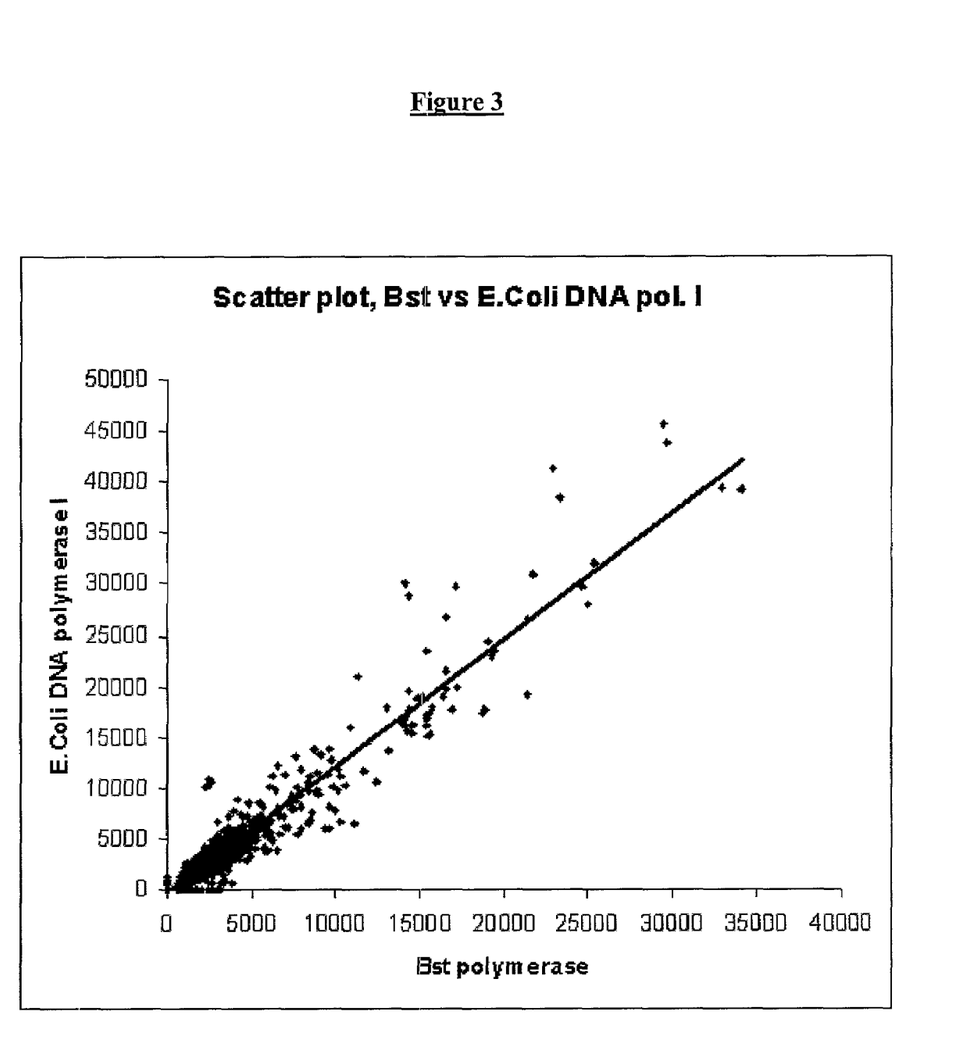
FIG. 3: Scatter plot of raw microarray data from RNA amplified with one round of T7 amplification using *E. coli* DNA polymerase I or Bst DNA polymerase large fragment for second strand synthesis. The correlation coefficient $R^2=0.92$.

Data from aRNA generated by one round of T7 amplification using Bst polymerase in the second strand cDNA synthesis step was compared to data generated using $E.$ $Coli$ DNA polymerase I for second strand cDNA synthesis. Comparison was done by scatter plot (FIG. 3). The overall correlation ($R^2$) in intensity for individual clones on the microarray was greater then 0.92, indicating that the gene expression patterns generated by using either Bst polymerase or $E.$ $Coli$ DNA polymerase I are quite similar.

What is claimed is:

1. A method for amplifying at least one mRNA in a sample containing a plurality of different mRNAs comprising:
   a) synthesizing first strand cDNA by contacting under conditions conducive to reverse transcriptase activity at least one mRNA in said sample with (i) reverse transcriptase, and (ii) a first primer that is sufficiently complementary to a sequence in the mRNA so as to prime synthesis in a direction toward the 5' end of the mRNA;
   b) synthesizing a second strand of cDNA by contacting under conditions conducive to a thermostable DNA polymerase activity, said conditions comprising an incubation temperature of from 55° C. to 70° C., the first strand cDNA with (i) a thermostable DNA polymerase, which is Bst DNA polymerase large fragment, and (ii) a thermostable RNase H, thereby forming double stranded cDNA; and
   c) transcribing the double stranded cDNA into cRNA by contacting the double stranded cDNA with an RNA polymerase under conditions conducive to RNA polymerase activity, such that cRNA is produced.

2. The method of claim 1 wherein said incubation temperature is from 60° C. to 65° C.

3. The method of claim 1 wherein the conditions for synthesizing the second strand of cDNA further comprise an incubation time of from one to sixty minutes.

4. The method of claim 1, which further comprises labeling the transcribed cRNA with a fluorescent, radioactive, enzymatic, hapten, biotin, or digoxigenin label.

5. The method of claim 1, wherein the thermostable Bst DNA polymerase large fragment is present in a concentration of from 0.012 to 1.3 units/µl and the thermostable RNase H is present in a concentration of from 0.0031 to 1.3 units/µl.

6. The method of claim 4, wherein the label is fluorescent.

7. The method of claim 6 wherein the fluorescent label is fluorescein isothiocyanate, lissamine, Cy3, Cy5, or rhodamine 110.

8. The method of claim 6, wherein a first aliquot of the cRNA is labeled with a first fluorophore having a first emission spectrum, and a second aliquot of the cRNA is labeled with a second fluorophore with a second emission spectrum differing from that of the first emission spectrum.

9. The method of claim 8, wherein the first fluorophore is Cy3 and the second fluorophore is Cy5.

10. The method of claim 1 further comprising, after the transcribing step, determining the presence or absence of a pre-selected target mRNA in said sample.

11. The method of claim 1, wherein the conditions for synthesizing the second strand of cDNA further comprise an incubation time of from five to thirty minutes.

12. The method of claim 1, wherein the mRNA is extracted from at least one cell of interest, and further comprising contacting the cRNA produced in step (c) with an away containing one or more species of polynucleotide positioned at pre-selected sites on the affay, under conditions conducive to hybridization; and detecting any hybridization that occurs between said one or more species of polynucleotide and said cRNA.

13. A method for comparing the presence or amount of at least one mRNA of interest in a first sample and in a second sample, said first sample and said second sample each containing a plurality of different mRNAs from one or more cells, comprising:
   a) synthesizing first strand cDNA by contacting under conditions conducive to reverse transcriptase activity at least one mRNA in said first sample with (i) reverse transcriptase, and (ii) a first primer that is sufficiently complementary to a sequence in the mRNA so as to prime synthesis in a direction toward the 5' end of the mRNA;
   b) synthesizing a second strand of cDNA by contacting, under conditions conducive to thermostable DNA polymerase activity, said conditions comprising an incubation temperature of from 55° C. to 70° C., the first strand cDNA with (i) a thermostable DNA polymerase, which is Bst DNA polymerase large fragment, and (ii) a thermostable RNase H, thereby forming double stranded cDNA;
   c) transcribing the double stranded cDNA into cRNA by contacting the double stranded cDNA with an RNA polymerase under conditions conducive to RNA polymerase activity, such that cRNA is produced;
   d) labeling the cRNA produced in step (c) with a first label;
   e) repeating steps (a)-(c) with said second sample;
   f) labeling the cRNA produced in step (e) with a second label distinguishable from said first label;
   g) detecting or measuring the mRNA of interest in the first sample by contacting the cRNA labeled with said first label with a polynucleotide capable of hybridizing to said cRNA of the mRNA of interest under conditions conducive to hybridization; and detecting any hybridization that occurs between said polynucleotide and said cRNA;
   h) detecting or measuring the mRNA of interest in the second sample by contacting the cRNA labeled with said second label with said polynucleotide capable of hybridizing to said cRNA of the mRNA of interest under conditions conducive to hybridization; and detecting any hybridization that occurs between said polynucleotide and said cRNA; and
   i) comparing the mRNA of interest detected or measured in said first sample with the mRNA of interest detected or measured in said second sample.

14. The method of claim 13 wherein said sample contains total RNA or total mRNA from mammalian cells.

15. The method of claim 13 wherein the incubation temperature is from 60° C. to 65° C.

16. The method of claim 13 wherein said first label is Cy3 and said second label is Cy5.

17. The method of claim 13 wherein said detecting or measuring steps (g) and (h) are canied out by a method comprising contacting said cRNA with an array containing one or more species of polynucleotide positioned at pre-selected sites on the array, under conditions conducive to hybridization; and detecting any hybridization that occurs between said polynucleotide and said cRNA.

18. The method of claim 17 wherein the array comprises a support with at least one surface and more than one different polynucleotides, each different polynucleotide comprising a different nucleotide sequence and being attached to the surface of the support in a different, selected location on said surface.

19. The method of claim 17 wherein the array has at least 1,000 polynucleotide probes per square centimeter.

20. The method of claim 13 wherein in steps (g) and (h), the steps of contacting the cRNA labeled with said first label with said polynucleotide probe, and contacting the cRNA labeled with said second label with said polynucleotide probe, are carried out concurrently.

21. The method of claim 13 wherein said first sample contains mRNAs from cells that are pathologically aberrant and wherein said second sample contains mRNAs from cells that are not pathologically aberrant.

* * * * *

UNITED STATES PATENT AND TRADEMARK OFFICE
CERTIFICATE OF CORRECTION

PATENT NO. : 7,354,742 B2
APPLICATION NO. : 10/080795
DATED : April 8, 2008
INVENTOR(S) : Fredrik Kamme et al.

It is certified that error appears in the above-identified patent and that said Letters Patent is hereby corrected as shown below:

Title Page,
Col. 1, line 6, Item (56) References Cited:
OTHER PUBLICATIONS
"Chirgwin et al.," reference, delete ""Idolation" and insert -- "Isolation --.

Column 2,
Line 61, after "variability" insert -- . --.

Column 3,
Line 38, delete "(ii)" (second occurrence).
Lines 42-43, delete "thermosilable" and insert -- thermostable --.

Column 9,
Line 11, delete "11 g" and insert -- 1 µg --.

Column 13,
Line 60, delete "$2_{nd}$" and insert -- $2^{nd}$ --.

Column 20,
Line 22, delete "lug" and insert -- 1 µg --.

Column 26,
Line 9, delete "75-percertilc" and insert -- 75-percentile --.

Column 27,
Line 56, delete "away" and insert -- array --.
Line 57, delete "affay," and insert -- array, --.

Signed and Sealed this

Sixth Day of April, 2010

David J. Kappos
*Director of the United States Patent and Trademark Office*